(12) United States Patent
Sugar (10) Patent No.: US 10,514,368 B2
(45) Date of Patent: Dec. 24, 2019

(54) APPARATUS FOR PREVENTING CARBON MONOXIDE POISONING IN PASSENGER VEHICLES

(71) Applicant: Grant Sugar, Dublin, OH (US)

(72) Inventor: Grant Sugar, Dublin, OH (US)

( * ) Notice: Subject to any disclaimer, the term of this patent is extended or adjusted under 35 U.S.C. 154(b) by 0 days.

(21) Appl. No.: 15/954,071

(22) Filed: Apr. 16, 2018

(65) Prior Publication Data

US 2018/0348182 A1 Dec. 6, 2018

Related U.S. Application Data

(60) Provisional application No. 62/485,412, filed on Apr. 14, 2017.

(51) Int. Cl.
*G01N 33/00* (2006.01)
*G08B 21/14* (2006.01)

(52) U.S. Cl.
CPC ....... *G01N 33/004* (2013.01); *G01N 33/0073* (2013.01); *G08B 21/14* (2013.01)

(58) Field of Classification Search
CPC ... G01N 33/004; G01N 33/0073; G08B 21/14
See application file for complete search history.

(56) References Cited

U.S. PATENT DOCUMENTS

| | | | | |
|---|---|---|---|---|
| 8,354,935 | B2* | 1/2013 | Rauworth | G08B 29/181 340/522 |
| 8,803,677 | B1* | 8/2014 | Miller | G08B 21/14 340/438 |
| 2007/0120693 | A1* | 5/2007 | Vij | G08B 21/14 340/632 |
| 2012/0229286 | A1* | 9/2012 | Rauworth | G08B 29/181 340/632 |
| 2012/0310547 | A1* | 12/2012 | Cristoforo | G08B 21/14 702/24 |
| 2015/0079697 | A1* | 3/2015 | Belbruno | G01N 27/126 436/501 |
| 2015/0356863 | A1* | 12/2015 | Bartenwerfer | G08B 25/009 340/436 |

* cited by examiner

*Primary Examiner* — Sisay Yacob
(74) *Attorney, Agent, or Firm* — Standley Law Group LLP; Eric M. Gayan; Stephen L. Grant (57) ABSTRACT

Exemplary embodiments described and shown herein generally relate to apparatus for detecting the level of carbon monoxide (CO) present in a passenger vehicle. Some embodiments may interface with standard 12 volt vehicle power outlets or with USB power outlets, while others may be designed to be hard-wired into a vehicle electrical system. An audible alarm, warning light, and/or display may be used to warn a passenger that CO levels are concerning or dangerous. In some embodiments, an engine kill switch may be included and activated when certain CO levels are detected from some period of time. Threat levels and corresponding time thresholds may be stored and used to determine when a warning should be issued.

19 Claims, 10 Drawing Sheets

APPARATUS FOR PREVENTING CARBON MONOXIDE POISONING IN PASSENGER VEHICLES

CROSS-REFERENCE TO RELATED APPLICATIONS

This application claims the benefit of U.S. Provisional Application No. 62/485,412 filed on Apr. 14, 2017, which is hereby incorporated by reference as if fully recited herein.

TECHNICAL FIELD

Exemplary embodiments described and shown herein generally relate to apparatus for detecting the level of carbon monoxide present in a passenger vehicle.

BACKGROUND

Vehicle-related carbon monoxide emissions continue to harm the public, either through inadvertent leaks from old exhaust systems or damaged exhaust systems, or through purposeful inhalation of vehicle exhaust fumes by individuals attempting suicide through asphyxiation. When inhaled for even a short period of time, the repercussions can be fatal. Persons with breathing problems, such as asthma or a diminished lung capacity, can be especially sensitive to carbon monoxide leaks. While most gases can be detected either through sight or smell, carbon monoxide is colorless, odorless, and tasteless. There exists an increased need for devices to help prevent deaths or health complications due to carbon monoxide exposure.

Older vehicles, classic vehicles, or vehicles subject to damage from "off-roading" can be susceptible to carbon monoxide leaks without the drivers/passengers being aware of the risk. Further, passengers can now hail a ride from various applications on their mobile phones, which result in a ride from an unknown private individual in a car with an unknown maintenance record. For those who are sensitive to carbon monoxide levels generally, they could be stepping into a vehicle that is long overdue for an exhaust repair, and without being aware of the situation at hand, they could be subjecting themselves to serious injury.

SUMMARY OF THE EXEMPLARY EMBODIMENTS

Exemplary embodiments presented herein provide an apparatus for detecting the carbon monoxide (CO) level inside the passenger compartment of a passenger vehicle such as, but not limited to, an automobile. Some embodiments can plug into 12 volt power outlets or USB power outlets, while others may be designed to be hard-wired into a vehicle electrical system. An audible alarm, warning light, and/or display may be used to warn a passenger that CO levels are concerning or dangerous. In some embodiments, high levels of CO may cause the apparatus to initiate a combustion engine kill switch that would stop operations of the combustion engine when threatening high levels of CO are measured.

The foregoing and other features and advantages of the present invention will be apparent from the following more detailed description of the particular exemplary embodiments, as illustrated in the accompanying drawings.

BRIEF DESCRIPTION OF THE DRAWINGS

A better understanding of an exemplary embodiment will be obtained from a reading of the following detailed description and the accompanying drawings wherein identical reference characters refer to identical parts and in which.

DETAILED DESCRIPTION OF EXEMPLARY EMBODIMENTS

The inventive concept is described more fully hereinafter with reference to the accompanying drawings, in which exemplary embodiments are shown. This inventive concept may, however, be embodied in many different forms and should not be construed as limited to the specific exemplary embodiments set forth herein. Rather, the exemplary embodiments are provided in an attempt to thoroughly and completely convey the inventive concept to those of skill in the art. In the drawings, the size and relative sizes of layers and/or regions may be exaggerated for clarity.

The terminology used herein is for the purpose of describing particular exemplary embodiments only and is not intended to be limiting of the inventive concept. As used herein, the singular forms "a", "an" and "the" are intended to include the plural forms as well, unless the context clearly indicates otherwise. It is to be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Exemplary embodiments are described herein with reference to schematic illustrations. As such, variations from the shapes of the illustrations as a result, for example, of manufacturing techniques and/or tolerances, are to be expected. The exemplary embodiments should not, therefore, be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
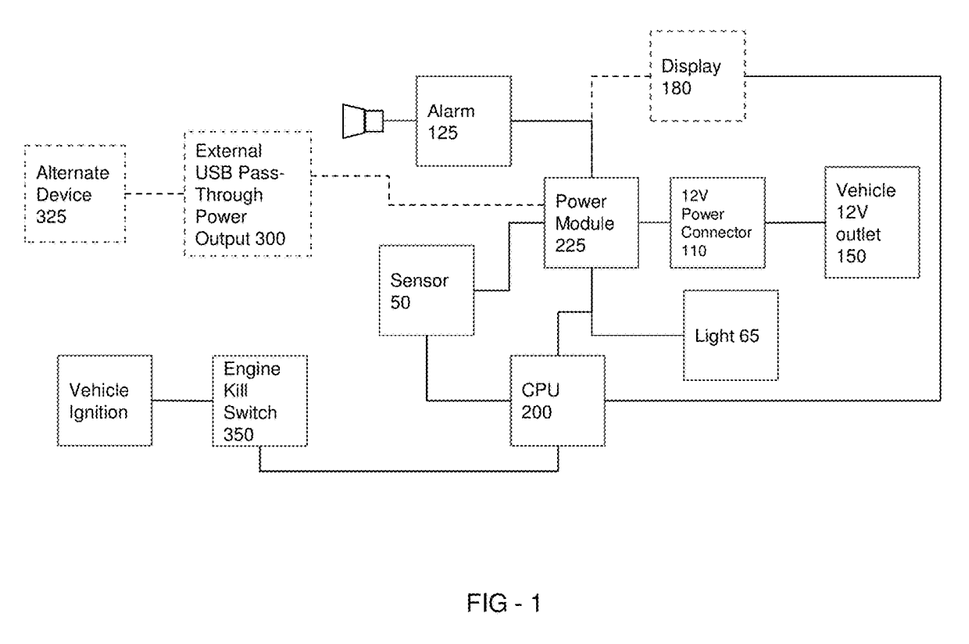
FIG. 1 is an electrical block diagram of one exemplary embodiment of a 12 volt plug-in carbon monoxide detecting apparatus.

FIG. 1 is an electrical block diagram of one exemplary embodiment of a carbon monoxide detecting apparatus that is designed to plug in to a standard 12 volt outlet in a vehicle. The device obtains power from the 12 volt outlet 150 of the vehicle, through a 12 volt power connector 110, which is in electrical connection with a power module 225. An audible alarm 125, light 65, and carbon monoxide sensor 50 are preferably in electrical connection with the power module 225. A CPU 200 is preferably in electrical connection with the power module 225 and the sensor 50, and is capable of performing any of the logic that is shown and described in this application. The CPU 200 should include a microprocessor and electronic storage (memory), which may be integral or separate from the microprocessor. An optional display 180 may also be placed in electrical connection with the power module 225 and/or the CPU 200.

An optional external USB pass-through power output 300 may also be in electrical connection with the power module 225. The USB pass-through power output 300 may be connected with a separate device 325 such that the carbon monoxide apparatus may operate while simultaneously also powering the separate device 325.

Figure 2:
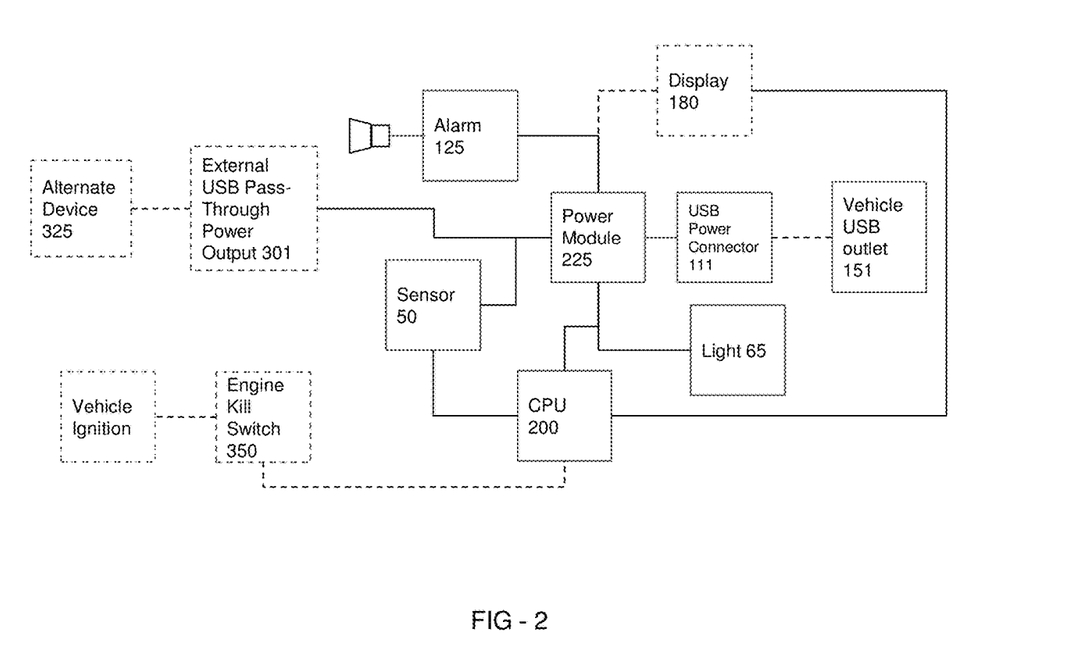
FIG. 2 is an electrical block diagram of an exemplary embodiment of a carbon monoxide detecting apparatus that is compatible with a traditional USB power connection.

FIG. 2 is an electrical block diagram of another exemplary embodiment of a carbon monoxide detecting apparatus that is compatible with a traditional USB power connection 151. Such USB power connections are commonly found in modern vehicles, and may be added to older vehicles. This exemplary embodiment is substantially similar to the exemplary embodiment shown in FIG. 1, with a notable exception being that the carbon monoxide detecting apparatus of FIG. 2 is powered from the USB connection 151 using a USB power connector 111, versus from the traditional 12 volt outlet 150 using the 12 volt power connector 110.

An optional external USB pass-through power output 301 may also be in electrical connection with the power module 225 in this exemplary embodiment. The USB pass-through power output 301 may again be connected with a separate device 325 such that the carbon monoxide apparatus may operate while simultaneously also powering the separate device 325.

Figure 3:
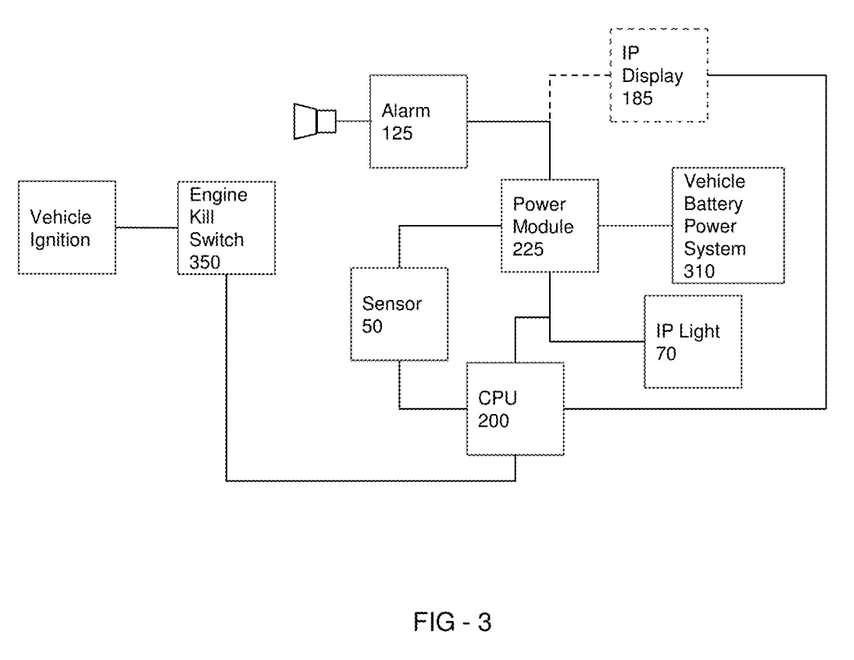
FIG. 3 is an electrical block diagram of an exemplary carbon monoxide detecting apparatus that is designed to be hard-wired into a vehicle electrical system.

FIG. 3 is an electrical block diagram of an exemplary carbon monoxide detecting apparatus that is configured for hard wiring to a vehicle electrical system 300. Many of the components of this exemplary embodiment are again substantially similar to those shown and described above, with a notable difference being that the apparatus of FIG. 3 obtains power directly from the power system 310 of the vehicle. In some embodiments, the apparatus may obtain power from the vehicle through, for example, an existing vehicle fuse block. The power module 225, sensor 50, and CPU 200 of the apparatus could be placed anywhere within the vehicle, such as the instrument panel, etc.

In this particular exemplary embodiment, a light 70 as well as an optional display 185 are placed on the instrument panel of the vehicle. An optional engine kill switch 350 is also provided in this exemplary embodiment, and is preferably electrically connected with both the CPU 200 and the ignition of the vehicle, such that operation of the vehicle engine may be terminated by activation of the kill switch 350.

In an exemplary embodiment of a carbon monoxide detecting apparatus, a plurality of Threat Levels (TLs) may be created for various concentrations of carbon monoxide that are measured in the air, with corresponding Time Thresholds (TTs) for measurements within a particular Threat Level. For example, Table 1 provides one possible arrangement,

TABLE 1

| Threat Level (TL) | CO ppm | Time Threshold (TT) |
|---|---|---|
| 1 | 250-800 ppm | 30 min |
| 2 | 801-1,600 ppm | 15 min |
| 3 | 1,601-3,200 ppm | 10 min |
| 4 | 3,201-6,400 ppm | 5 min |
| 5 | 6,401 and above | 30 seconds |

Figure 4:
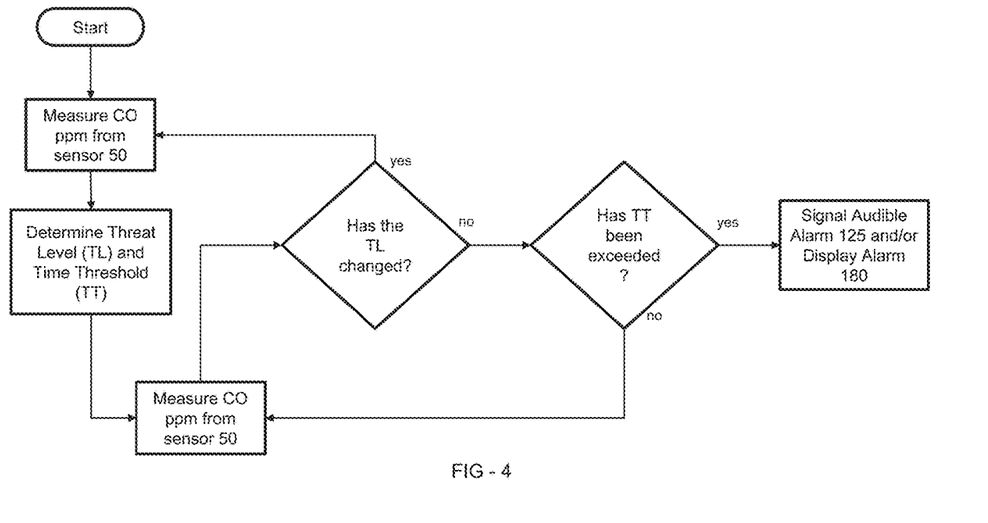
FIG. 4 is a logical flowchart showing one embodiment for the operation of the CPU shown in FIGS. 1 and 2.

FIG. 4 is a logical flowchart describing the operation of the CPU 200 shown in the block diagrams of FIGS. 1 and 2 and incorporating Threat Levels and Time Thresholds such as those shown in Table 1. Initially, the apparatus measures the CO amounts from the sensor 50 and determines the Threat Level and Time Threshold for the given CO amount. The apparatus then re-measures the CO amount from the sensor 50 and determines if the Threat Level has changed, and if so, returns to re-measure the CO amount and determine the new Threat Level. If the Threat Level has not changed, the apparatus determines if the Time Threshold for the determined Threat Level has been exceeded. If the Time Threshold has not been exceeded, the apparatus continues to re-measure the CO amount and reassess the Threat Level. If the Time Threshold has been exceeded at any point, the apparatus signals the audible alarm 125 and/or the display alarm 180.

Figure 5:
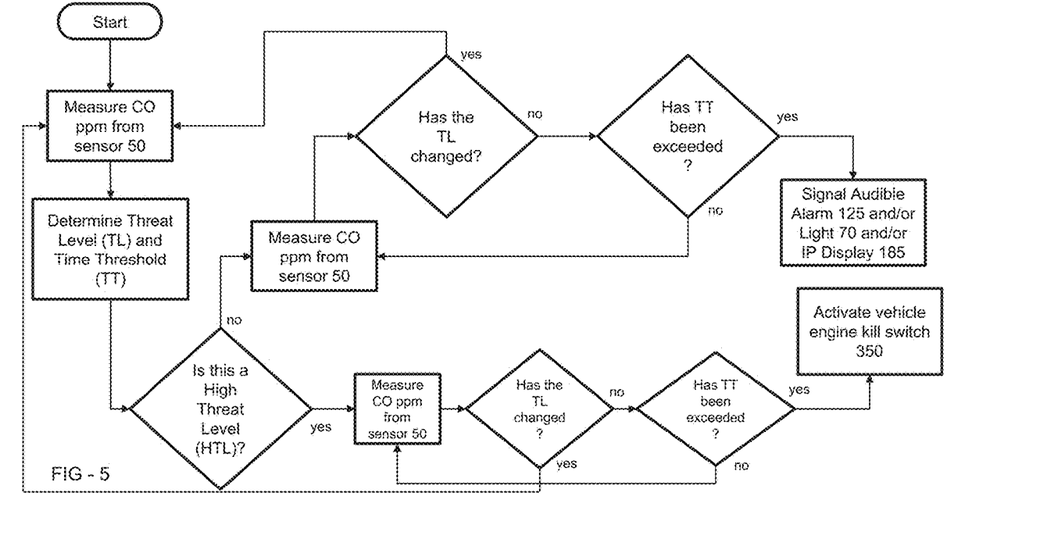
FIG. 5 is a logical flowchart showing one embodiment for the operation of the CPU in FIG. 3.

FIG. 5 is a logical flowchart describing the operation of the CPU 200 shown in the block diagram of FIG. 3 and incorporating Threat Levels and Time Thresholds such as those shown in Table 1. In this embodiment, a High Threat Level (HTL) may be defined as some measured CO concentration level within a vehicle that may be indicative of a possible suicide attempt or the imminent threat of serious bodily harm to occupants of the vehicle. Using the exemplary Threat Levels and Time Thresholds of Table 1 above, the High Threat Level may be set to coincide with, for example, any measured CO level that equals or exceeds the CO level associated with Threat Level 5. Thus, in operation of this exemplary embodiment, once the CO level has been measured, the apparatus can determine whether or not the current CO level constitutes a High Threat Level. If the apparatus determines that the current CO level does not constitute a High Threat Level, then operation would proceed similarly to the operation described above with respect to the exemplary logic of FIG. 5. That is, the apparatus will proceed to remeasure the CO amount to ensure that the Threat Level has not changed and will continue checking to see if the Time Threshold has been exceeded, at which point the system would signal the audible alarm 125 and/or the display alarm 180.

However, according to the logic of FIG. 5, if the exemplary apparatus determines that the current Threat Level is a High Threat Level, the CO amount is re-measured to determine if the High Threat Level remains and the Time Threshold is associated with the High Threat Level is continually re-checked. If it is determined that a High Threat Level remains and the associated Time Threshold has been exceeded, vehicle engine operation is terminated via initiation of the engine kill switch 350.

Figure 6:
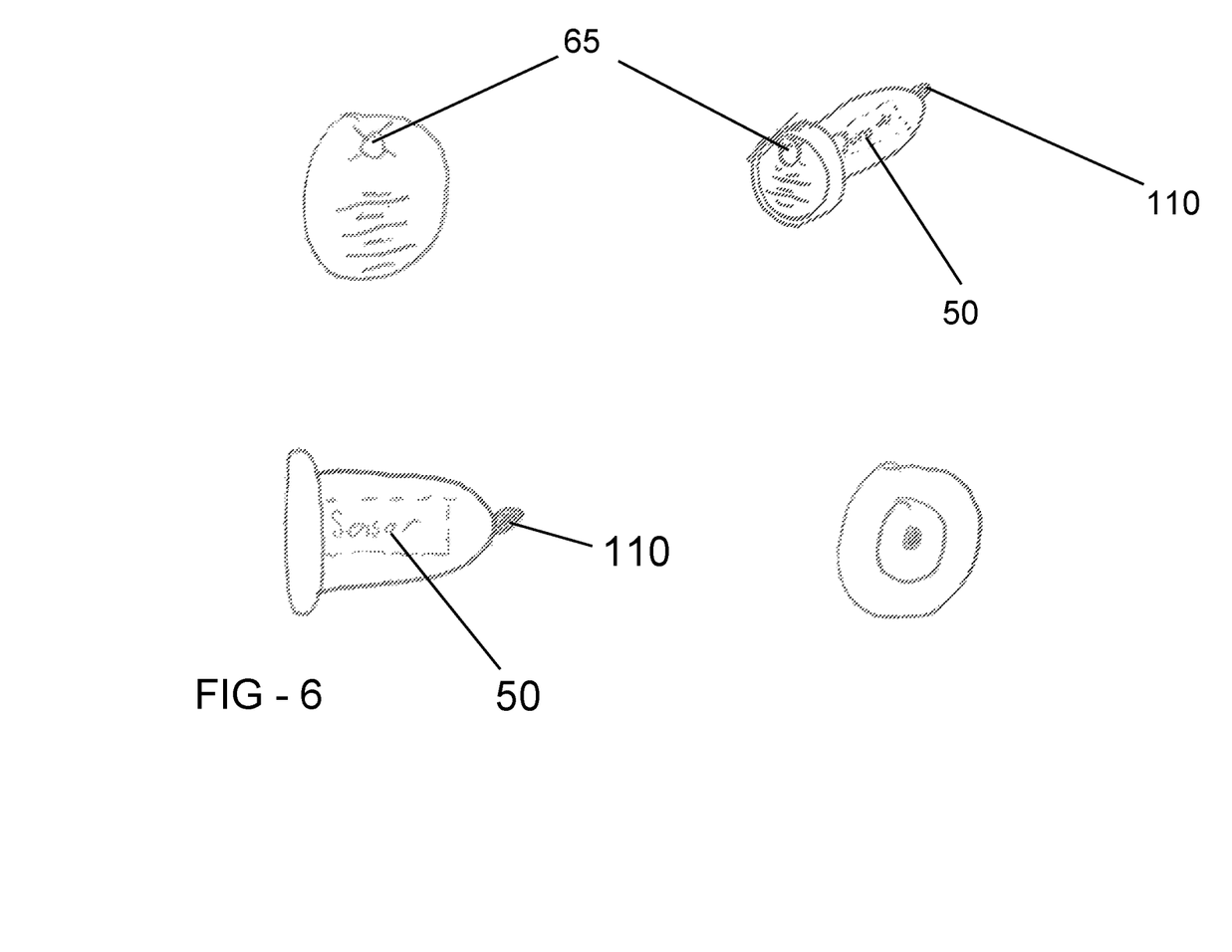
FIG. 6 depicts one exemplary embodiment of a carbon monoxide detecting apparatus utilizing the electrical circuitry and logic of FIGS. 1 and 4, without the optional external USB pass-through power output.

FIG. 6 depicts one exemplary embodiment of a carbon monoxide detecting apparatus utilizing the electrical circuitry and logic of FIGS. 1 and 4. As indicated, the apparatus includes a body and a power connector that are configured to plug-in to a traditional 12 volt vehicle outlet. In this embodiment, the optional external USB pass-through power output 300 of FIG. 1 is omitted.

Figure 7:
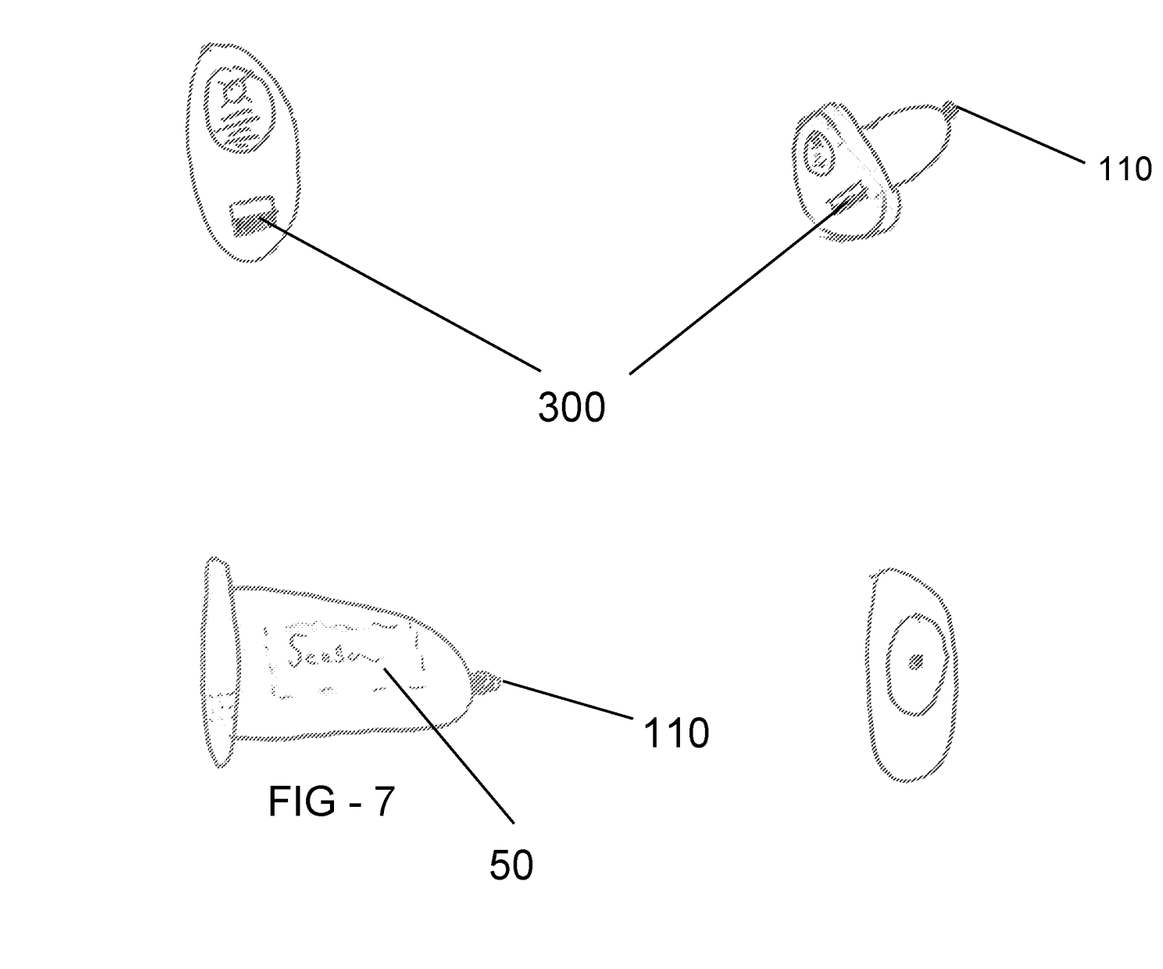
FIG. 7 depicts another exemplary embodiment of a carbon monoxide detecting apparatus utilizing the electrical circuitry and logic of FIGS. 1 and 4, with the optional external USB pass-through power output.

FIG. 7 depicts one exemplary embodiment of a carbon monoxide detecting apparatus utilizing the electrical circuitry and logic of FIGS. 1 and 4. As indicated, the apparatus again includes a body and a power connector that are configured to plug-in to a traditional 12 volt vehicle outlet 150. In this embodiment, however, the optional external USB pass-through power output 300 of FIG. 1 is present.

Figure 8:
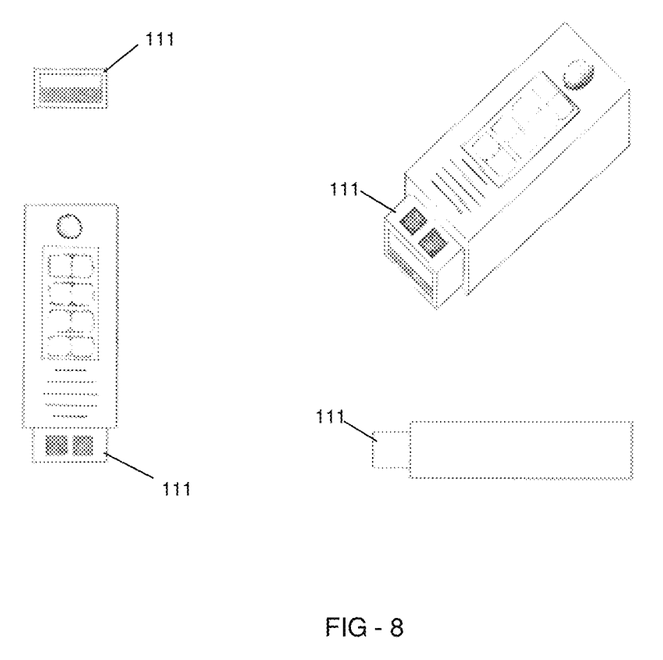
FIG. 8 depicts one exemplary embodiment of a carbon monoxide detecting apparatus utilizing the electrical circuitry and logic of FIGS. 2 and 4.

FIG. 8 depicts one exemplary embodiment of a carbon monoxide detecting apparatus utilizing the electrical circuitry and logic of FIGS. 2 and 4. In this exemplary embodiment, the apparatus is designed to receive power via a USB connection. To this end, the apparatus includes a body having a USB power connection 111 that is configured to plug into a USB power outlet 151 of a vehicle.

Figure 9:
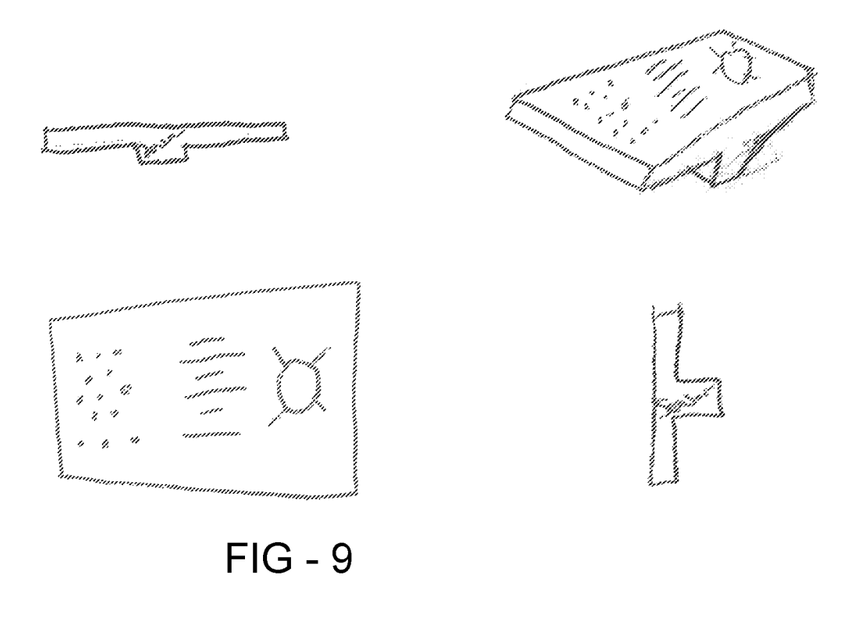
FIG. 9 depicts one exemplary embodiment of a carbon monoxide detecting apparatus utilizing the electrical circuitry and logic of FIGS. 3 and 5.

FIG. 9 depicts one exemplary embodiment of a carbon monoxide detecting apparatus utilizing the electrical circuitry and logic of FIGS. 3 and 5. In this exemplary embodiment, the apparatus is configured for hard wiring into the existing electrical system 300 of a vehicle. A vehicle engine kill switch 350 is also included as part of this exemplary apparatus, and is operable when the apparatus is properly wired to the vehicle to terminate operation of the vehicle's engine when certain conditions are sensed.

Figure 10:
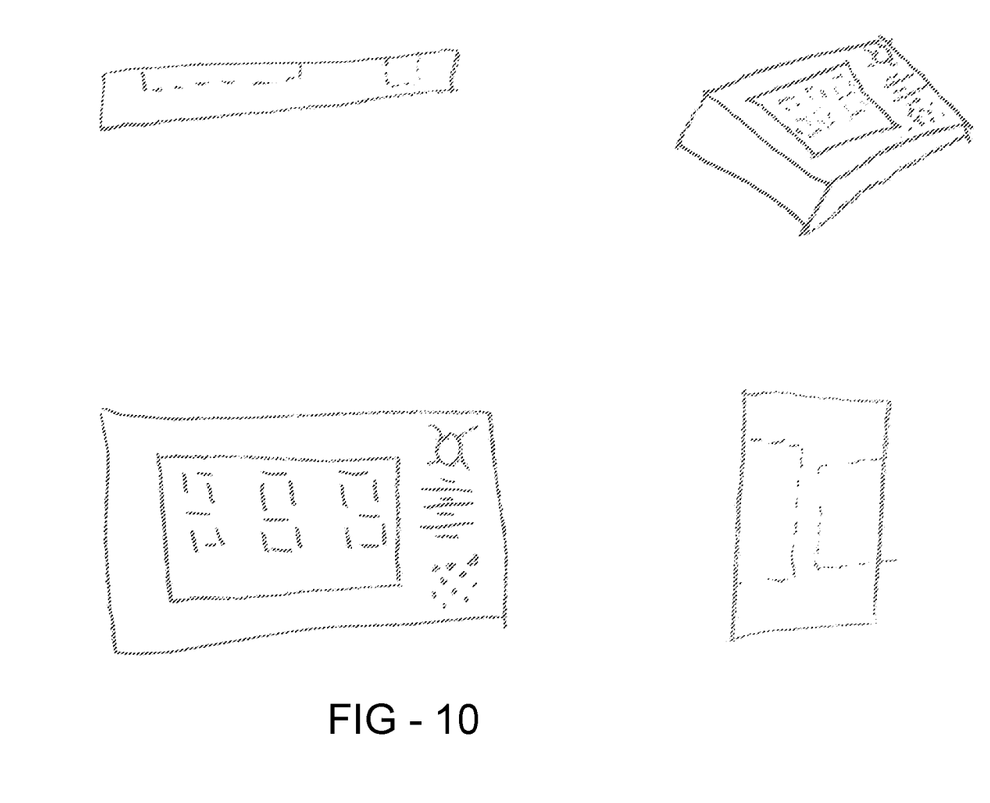
FIG. 10 depicts one exemplary embodiment of a carbon monoxide detecting apparatus utilizing the electrical circuitry and logic of FIGS. 3 and 5.

FIG. 10 depicts another exemplary embodiment of a carbon monoxide detecting apparatus utilizing the electrical circuitry and logic of FIGS. 3 and 5. In this exemplary embodiment, the apparatus is configured substantially similarly to the embodiment of FIG. 9, but also includes an onboard digital display.

Although not required, the displays shown and described herein with respect to various exemplary embodiments are preferably LED backlit digital displays, but could also be OLED displays or any other electroluminescent polymer. Further, the lights shown and described herein are preferably LED lights. The lights may be of various color and intensity, but should be easy to see. For example, the lights may be red in color and may have an output of at least 8 lumens.

Having shown and described various exemplary embodiments of the inventive concept, those skilled in the art will realize that many other variations and modifications may be made while remaining within the scope of the inventive concept. Additionally, many of the elements indicated above may be altered or replaced by different elements that will provide the same result and fall within the spirit of the inventive concept. It is the intention, therefore, to limit the inventive concept only as indicated in the claims.

What is claimed is:

1. An apparatus for detecting the carbon monoxide level within a passenger vehicle, comprising:
   a body having a power connector located thereon, the power connector configured to plug in to a standard USB outlet;
   electronics including at least a power module, a microprocessor, electronic memory and a carbon monoxide sensor arranged at least partially within the body, the electronics configured to operate on USB-level power; and
   indicator means for warning a vehicle passenger when certain carbon monoxide levels are present within the vehicle;
   wherein the microprocessor is programmed to cause the carbon monoxide sensor to repeatedly measure the carbon monoxide level within the vehicle and, when a detected carbon dioxide level exists for more than some corresponding predetermined period of time, to activate the indicator means.

2. The apparatus of claim 1, further comprising a pass-through USB connector via which a separate USB-powerable device may be powered simultaneously with the apparatus.

3. The apparatus of claim 1, further comprising at least one indicator means that is in communication with but locatable remotely from the body.

4. The apparatus of claim 1, wherein the indicator means is selected from the group consisting of a light, an audible alarm, a graphic display, and combinations thereof.

5. The apparatus of claim 1, further comprising a vehicle engine kill switch, the kill switch in electrical communication with the microprocessor and configured for electrical connection to an ignition system of the vehicle.

6. The apparatus of claim 5, wherein the microprocessor is programmed to activate the kill switch when a certain carbon monoxide level is detected for more than a corresponding time threshold.

7. The apparatus of claim 1, wherein various threat levels and corresponding time thresholds relative to different carbon monoxide levels are stored in the electronic memory.

8. The apparatus of claim 7, wherein the microprocessor is further programmed to correlate a measured carbon monoxide level within the vehicle with a stored threat level, and when said threat level exists for more than a corresponding period of time, to activate the indicator means.

9. The apparatus of claim 1, wherein the memory is integral to the microprocessor.

10. An apparatus for detecting the carbon monoxide level within a passenger vehicle, comprising:
    a body;
    electronics including at least a power module, a microprocessor, electronic memory and a carbon monoxide sensor arranged at least partially within the body;
    a power connector located on the body;
    indicator means for warning a vehicle passenger when certain carbon monoxide levels are present within the vehicle;
    a vehicle engine kill switch, the kill switch in electrical communication with the microprocessor and configured for electrical connection to an ignition system of the vehicle;
    wherein the microprocessor is programmed to cause the carbon monoxide sensor to repeatedly measure the carbon monoxide level within the vehicle and, when a detected carbon dioxide level exists for more than some corresponding predetermined period of time, to activate the indicator means.

11. The apparatus of claim 10, wherein the body and power connector are configured to plug in to a standard 12 volt vehicle outlet, and the electronics are configured to operate on 12 volt power.

12. The apparatus of claim 10, further comprising a pass-through USB connector via which a separate USB-powerable device may be powered simultaneously with the apparatus.

13. The apparatus of claim 10, wherein the body and power connector are configured for hard wiring to an existing electrical system of the vehicle.

14. The apparatus of claim 10, further comprising at least one indicator means that is in communication with but locatable remotely from the body.

15. The apparatus of claim 10, wherein the indicator means is selected from the group consisting of a light, an audible alarm, a graphic display, and combinations thereof.

16. The apparatus of claim 10, wherein the microprocessor is programmed to activate the kill switch when a certain carbon monoxide level is detected for more than a corresponding time threshold.

17. The apparatus of claim 10, wherein various threat levels and corresponding time thresholds relative to different carbon monoxide levels are stored in the electronic memory.

18. The apparatus of claim 17, wherein the microprocessor is further programmed to correlate a measured carbon monoxide level within the vehicle with a stored threat level, and when said threat level exists for more than a corresponding period of time, to activate the indicator means.

19. The apparatus of claim 10, wherein the memory is integral to the microprocessor.

\* \* \* \* \*